Figure 1:
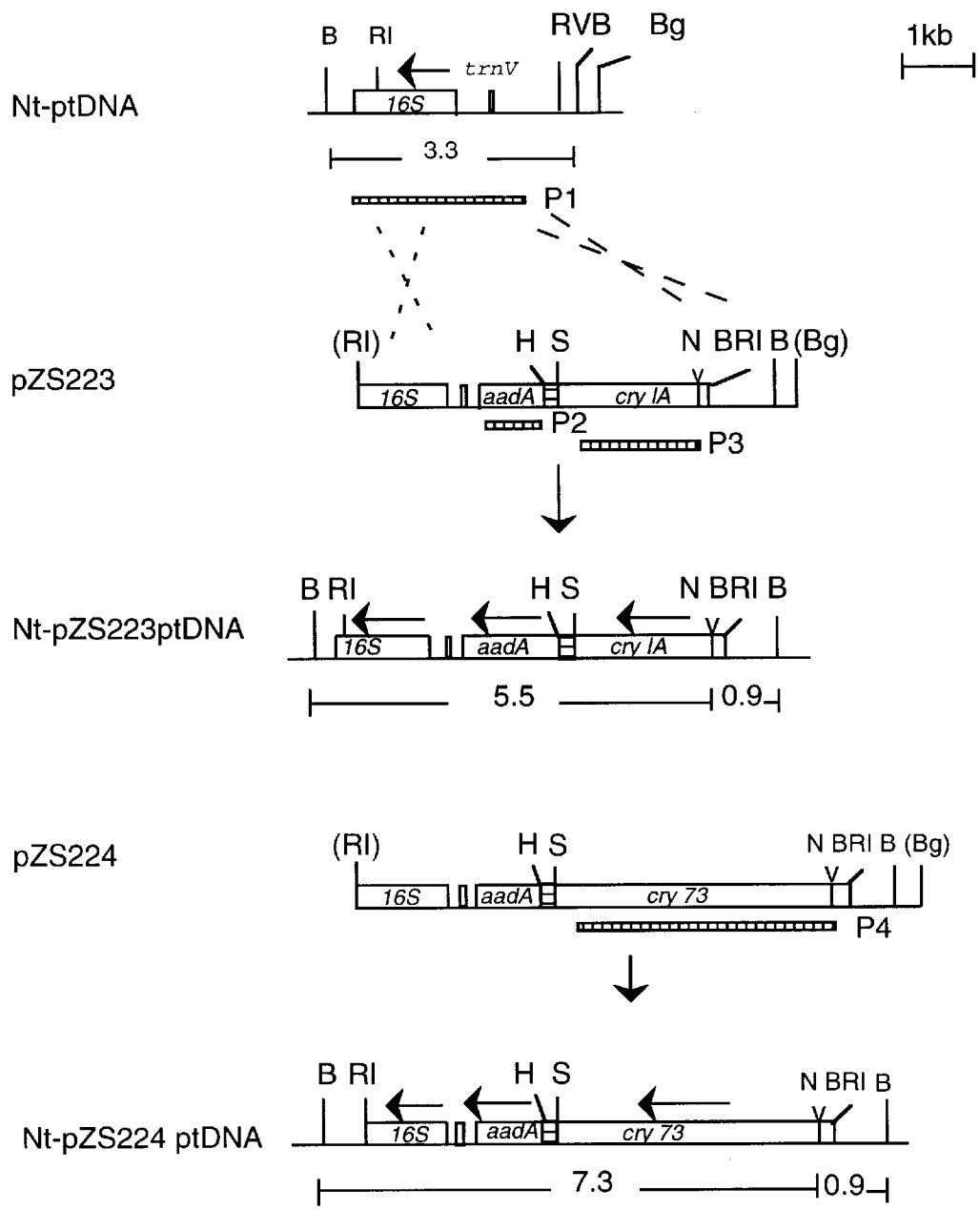

United States Patent [19]

McBride et al.

[11] Patent Number: 5,866,421

[45] Date of Patent: *Feb. 2, 1999

[54] ENHANCED EXPRESSION IN A PLANT PLASTID

[75] Inventors: Kevin E. McBride; David M. Stalker, both of Davis, Calif.

[73] Assignee: Calgene LLC, Davis, Calif.

[*] Notice: The term of this patent shall not extend beyond the expiration date of Pat. No. 5,545,817.

[21] Appl. No.: 593,205

[22] Filed: Jan. 29, 1996

Related U.S. Application Data

[63] Continuation of PCT/US95/02901, Mar. 10, 1995 which is a continuation-in-part of Ser. No. 209,649, Mar. 11, 1994, Pat. No. 5,545,817.

[51] Int. Cl.$^6$ .............................. C12N 5/14; C12N 15/82
[52] U.S. Cl. ....................... 435/419; 435/320.1; 435/440; 435/468
[58] Field of Search ........................... 800/205, DIG. 40, 800/43; 536/24.1; 435/320.1, 69, 240.4, 172.3, 70.1, 419, 172.1

[56] References Cited

U.S. PATENT DOCUMENTS 5,545,817  8/1996  McBride et al. ........................ 800/205

OTHER PUBLICATIONS

Koziel MG, et al. "Optimizing expression of transgenes with an emphasis on post–transcriptional events." Plant Mol. Biol. 32: 393–405, 1996.

*Primary Examiner*—Douglas W. Robinson
*Assistant Examiner*—Amy J. Nelson

[57] ABSTRACT

Novel compositions and methods useful for genetic engineering of plant cells to provide increased expression in the plastids of a plant or plant cell of a protein which produces a phenotype which is present when the plant or plant cell is grown in the absence of means for selecting transformed cells. Expression of the *Bacillus thuringiensis* bacterial protoxin in a plant chloroplast is exemplified.

9 Claims, 1 Drawing Sheet

– 5,866,421 –

SEQUENCE LISTING ( 1 ) GENERAL INFORMATION:

( i i i ) NUMBER OF SEQUENCES: 2

( 2 ) INFORMATION FOR SEQ ID NO: 1 :

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: synthetic oligonucleotide ( x i ) SEQUENCE DESCRIPTION: SEQ ID NO: 1 :

C C C G G A T C C A   T G G A T A A C A A   T C C G A A C A T C   A A T G A A T G C A   4 0

( 2 ) INFORMATION FOR SEQ ID NO: 2 :

(  i  ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: synthetic oligonucleotide ( x i ) SEQUENCE DESCRIPTION: SEQ ID NO: 2 :

TTCATTGATG TTCGGATTGT TATCCATGGA TCCGGG    36

ENHANCED EXPRESSION IN A PLANT PLASTID

INTRODUCTION

This application is a continuation of application PCT/US95/02901 filed Mar. 10, 1995 and a continuation-in-part of U.S. application Ser. No. 08/209,649 filed Mar. 11, 1994 issued as U.S. Pat. No. 5,545,817.

FIELD OF THE INVENTION

This invention relates to the application of genetic engineering techniques to plants. More specifically, the invention relates to compositions and methods for enhancing expression of a peptide of interest in the plastid of a plant cell.

BACKGROUND

Plastids of higher plants, i.e. chloroplasts, amyloplasts and chromoplasts, have the same genetic content, and thus are believed to be derived from a common precursor, known as a proplastid. The plastid genome is circular and varies in size among plant species from about 120 to about 217 kilobase pairs (kb). The genome typically includes a large inverted repeat, which can contain up to about 76 kilobase pairs, but which is more typically in the range of about 20 to about 30 kilobase pairs. The inverted repeat present in the plastid genome of various organisms has been described (Palmer, J. D. (1990) Trends Genet. 6:115–120).

One advantage of plant plastid transformation over nuclear transformation is that the plastids of most plants are maternally inherited, and consequently heterologous plastid genes are not pollen disseminated. This feature is particularly attractive for transgenic plants having altered agronomic traits, as introduced resistance or tolerance to natural or chemical conditions will not be transmitted to wild-type relatives.

Plant plastids are also major biosynthetic centers. In addition to photosynthesis in chloroplasts, plastids are responsible for production of important compounds such as amino acids, complex carbohydrates, fatty acids, and pigments.

Plastids can also express two or more genes from a single plastid promoter region. A DNA sequence expressed in a plastid may thus include a number of individual structural gene encoding regions under control of one set of regulatory components. Thus, it is possible to introduce and express multiple genes in a plant cell, either from an engineered synthetic sequence or from a pre-existing prokaryotic gene cluster.

Such an expression method makes possible large scale and inexpensive production of certain proteins and fine chemicals that are not practically produced through standard nuclear transformation methods. In nuclear expression from introduced genes, each encoding sequence must be engineered under the control of a separate regulatory region, i.e., a monocistron. As a consequence, gene expression levels vary widely among introduced sequences, and generation of a number of transgenic plant lines is required, with crosses necessary, to introduce all of the cistrons into one plant and to get proper coordinated expression in the target biochemical pathway.

Plastids can be present in a plant cell at a very high copy number, with up to 50,000 copies per cell present for the chloroplast genome (Bendich, A. J. (1987) BioEssays 6:279–282). Thus, through plastid transformation plant cells can be engineered to maintain an introduced gene of interest at a very high copy number.

For all of the above reasons, the plastids of higher plants present an attractive target for genetic engineering. Stable transformation of plastids has been reported in the green algae Chlamydomonas (Boynton et al. (1988) Science 240:1534–1538) and more recently in higher plants (Svab et al. (1990) Proc. Natl. Acad. Sci. USA 87:8526–8530: Svab and Maliga (1993) Proc. Natl. Acad. Sci. USA 90:913–917); (Staub, J. M. and Maliga, P. (1993), EMBO J. 12:601–606). The method disclosed for plastid transformation in higher plants relies on particle gun delivery of DNA containing a selectable marker and targeting of the DNA to the plastid genome through homologous recombination.

Many examples exist where expression levels greater than what is possible from nuclear expression would be desirable. One example can be found in those instances where it is desired to produce a novel substance in a mature plant for subsequent extraction and purification. Other examples of proteins which may need to be expressed at very high levels are those producing resistance or tolerance phenotypes in the plant. One example of such a phenotype is a toxin active against plant pests.

In particular, there is a continuing need to introduce newly discovered or alternative Bacillus thuringiensis genes into crop plants. Cry proteins (d-endotoxins) from Bacillus thuringiensis have potent insecticidal activity against a number of Lepidopteran, Dipteran, and Coleopteran insects. These proteins are classified CryI to CryV, based on amino acid sequence homology and insecticidal activity. Most CryI proteins are synthesized as protoxins (ca. 130–140 kDa) then solubilized and proteolytically processed into active toxin fragments (ca. 60–70 kDa).

The poor expression of the protoxin genes from the nucleus of plants has heretofore required the use of 'truncated' versions of these genes. The truncated versions code only for the active toxin fragments. Other attempts to increase the expression efficiency have included resynthesizing the Bacillus thuringiensis toxin genes to utilize plant preferred codons. Many problems can arise in such extensive reconstruction of these large cry genes (approximately 3.5 Kb), and the process is both laborious and expensive.

Problems can also arise as new insect pests become endemic, or as existing populations develop resistance to a particular level or type of Bacillus thuringiensis toxin. Thus, there is a particular need for producing higher and thereby more effective levels of the Bacillus thuringiensis toxin in plants, a need which will only increase with time.

SUMMARY OF THE INVENTION

By this invention, plastid expression constructs are provided which are useful for genetic engineering of plant cells and which provide for enhanced expression of a foreign peptide in plant cell plastids. The transformed plastid is preferably a metabolically active plastid, such as the chloroplasts found in green plant tissues including leaves or cotyledons. The plastid is preferably one which is maintained at a high copy number in the plant tissue of interest.

The plastid expression constructs for use in this invention generally include a plastid promoter region and a DNA sequence of interest to be expressed in transformed plastids. The DNA sequence of interest may be a single encoding region, or may contain a number of consecutive encoding regions, to be expressed as an operon, for example where introduction of a foreign biochemical pathway into plastids is desired.

In one embodiment, the DNA encoding sequence of the construct encodes the same amino acid sequence as the native DNA sequence, while having a codon usage enriched for adenine and thymine content. As an example, a native DNA sequence may be resynthesized to include an adenine and thymine content preferred by the plant plastid. While the adenine and thymine percentage content of the nuclear genome varies from organism to organism, in plants the codon utilization generally comprises more guanine and cytosine pairings than adenine and thymine, thus the content is considered enriched for guanine plus cytosine.

Plastid expression constructs of this invention may be linked to a construct having a DNA sequence encoding a selectable marker which can be expressed in a plant plastid. Expression of the selectable marker allows the identification of plant cells comprising a plastid expressing the marker.

In a preferred embodiment, transformation vectors for transfer of the construct into a plant cell include means for inserting the expression and selection constructs into the plastid genome. This preferably comprises regions of homology to the target plastid genome which flank the constructs.

Also by this invention a method is provided whereby a plastid expression construct is used to produce a peptide of interest in a plant cell. The peptide may be expressed in a plastid of the plant cell from the native DNA encoding sequence to the peptide. Alternatively, the DNA encoding sequence of the construct can be one enriched for adenine and thymine.

By this invention the insecticidal *Bacillus thuringiensis* toxin is produced in plastids of a plant cell from the native DNA encoding sequence, with enhanced levels of expression of an insect resistant phenotype, as measured by insect feeding assays. The native *Bacillus thuringiensis* DNA encoding sequence may be the truncated version specific to the active fragment. This invention also provides the expression of the *Bacillus thuringiensis* toxin from the non-truncated sequence which encodes the protoxin.

Plant cells and plants produced by a method of the invention and comprising a plastid expression construct are also considered in this invention.

DESCRIPTION OF THE FIGURES

FIG. 1 shows integration of cry genes from vectors pZS223 and pZS224 into the wild-type plastid genome (Nt-ptDNA) to yield transplastomes Nt-pZS223 ptDNA and Nt-pZS224 ptDNA, respectively.

DETAILED DESCRIPTION OF THE INVENTION

A plastid expression construct of this invention generally comprises a promoter functional in a plant plastid, a DNA sequence encoding a peptide of interest and a transcription termination region capable of terminating transcription in a plant plastid. These elements are provided as operably joined components in the 5' to 3' direction of transcription.

Any DNA encoding sequence which is enriched for adenine plus thymine content, and which can be inserted into the plastid genome of a plant cell to provide enhanced expression of a peptide of interest from the DNA encoding sequence, can be utilized.

In developing the constructs the various fragments comprising the regulatory regions and open reading frame may be subjected to different processing conditions, such as ligation, restriction enzyme digestion, PCR, in vitro mutagenesis, linkers and adapters addition, and the like. Thus, nucleotide transitions, transversions, insertions, deletions, or the like, may be performed on the DNA which is employed in the regulatory regions or the DNA sequences of interest for expression in the plastids. Methods for restriction digests, Klenow blunt end treatments, ligations, and the like are well known to those in the art and are described, for example, by Maniatis et al. (in *Molecular cloning: a laboratory manual* (1982) Cold Spring Harbor Laboratory Press, Cold Spring Harbor, N.Y.).

During the preparation of the constructs, the various fragments of DNA will often be cloned in an appropriate cloning vector, which allows for amplification of the DNA, modification of the DNA or manipulation of the DNA by joining or removing sequences, linkers, or the like. Preferably, the vectors will be capable of replication to at least a relatively high copy number in *E. coli.* A number of vectors are readily available for cloning, including such vectors as pBR322, vectors of the pUC series, the M13 series vectors, and pBluescript vectors (Stratagene; La Jolla, Calif.).

In order to provide a means of selecting the desired plant cells, vectors for plastid transformation typically contain a construct which provides for expression of a selectable marker gene. Marker genes are plant-expressible DNA sequences which express a polypeptide which resists a natural inhibition by, attenuates, or inactivates a selective substance, i.e., antibiotic, herbicide etc..

Alternatively, a marker gene may provide some other visibly reactive response, i.e., may cause a distinctive appearance or growth pattern relative to plants or plant cells not expressing the selectable marker gene in the presence of some substance, either as applied directly to the plant or plant cells or as present in the plant or plant cell growth media.

In either case, the plants or plant cells containing such selectable marker genes will have a distinctive phenotype for purposes of identification, i.e., they will be distinguishable from non-transformed cells. The characteristic phenotype allows the identification of cells, cell groups, tissues, organs, plant parts or whole plants containing the construct.

Detection of the marker phenotype makes possible the selection of cells having a second gene to which the marker gene has been linked. This second gene typically comprises a desirable phenotype which is not readily identifiable in transformed cells, but which is present when the plant cell or derivative thereof is grown to maturity, even under conditions wherein the selectable marker phenotype itself is not apparent.

The use of such a marker for identification of plant cells containing a plastid construct has been described. Svab et al. (1993 supra). In the examples provided below, a bacterial aada gene is expressed as the marker under the regulatory control of chloroplast 5' promoter and 3' transcription termination regions, specifically the tobacco 16S rRNA promoter rrn region and rps16 3' termination region. Numerous additional promoter regions may also be used to drive expression of the selectable marker gene, including various plastid promoters and bacterial promoters which have been shown to function in plant plastids.

Expression of the aadA gene confers resistance to spectinomycin and streptomycin, and thus allows for the identification of plant cells expressing this marker. The aadA gene product allows for continued growth and greening of cells whose chloroplasts comprise the selectable marker gene product. Cells which do not contain the selectable marker gene product are bleached. Selection for the aada gene marker is thus based on identification of plant cells which are not bleached by the presence of streptomycin, or more preferably spectinomycin, in the plant growth medium.

A number of markers have been developed for use with plant cells, such as resistance to chloramphenicol, the aminoglycoside G418, hygromycin, or the like. Other genes which encode a product involved in chloroplast metabolism may also be used as selectable markers. For example, genes which provide resistance to plant herbicides such as glyphosate, bromoxynil or imidazolinone may find particular use. Such genes have been reported (Stalker et al., *J. Biol. Chem.* (1985) 260:4724–4728 (glyphosate resistant EPSP); Stalker et al., *J. Biol. Chem.* (1985) 263:6310–6314 (bromoxynil resistant nitrilase gene); and Sathasivan et al., *Nucl. Acids Res.* (1990) 18:2188 (AHAS imidazolinone resistance gene)).

Stable transformation of tobacco plastid genomes by particle bombardment is reported (Svab et.al. (1990 supra) and Svab et al. (1993 supra)). The methods described therein may be employed to obtain plants homoplasmic for plastid expression constructs.

Generally, bombarded tissue is cultured for approximately 2 days on a cell division-promoting media, after which the plant tissue is transferred to a selective media containing an inhibitory amount of the particular selective agent, as well as the particular hormones and other substances necessary to obtain regeneration for that particular plant species. Shoots are then subcultured on the same selective media to ensure production and selection of homoplasmic shoots.

Homoplasmy is verified by southern analysis. In the examples provided below, BamHI-digested total cellular DNA is tested with various probes, specifically, a part of the plastid targeting fragment, an aadA fragment, a 1.8 kb cry1A fragment and a 3.5 kb fragment of the cry73 coding region. Southern blot analysis with these probes confirms the integration of the chimeric cry genes in the tobacco plastid genome to yield transplastome lines.

As an alternative to a second round of shoot formation, the initial selected shoots may be grown to mature plants and segregation relied upon to provide transformed plants homoplastic for the inserted gene construct.

Where transformation and regeneration methods have been adapted for a given plant species, either by Agrobacterium-mediated transformation, bombardment or some other method, the established techniques may be modified for use in selection and regeneration methods to produce plastid-transformed plants. For example, the methods described herein for tobacco are readily adaptable to other solanaceous species, such as tomato, petunia and potato.

In Brassica, Agrobacterium-mediated transformation and regeneration protocols generally involve the use of hypocotyl tissue, a non-green tissue which might contain a low plastid content. Thus, for Brassica, preferred target tissues would include microspore-derived hypocotyl or cotyledonary tissues (which are green and thus contain numerous plastids) or leaf tissue explants. While the regeneration rates from such tissues may be low, positional effects, such as seen with Agrobacterium-mediated transformation, are not expected, thus it would not be necessary to screen numerous successfully transformed plants in order to obtain a desired phenotype.

The vectors for use in plastid transformation preferably include means for providing a stable transfer of the plastid expression construct and selectable marker construct into the plastid genome. This is most conveniently provided by regions of homology to the target plastid genome. The regions of homology flank the construct to be transferred and provide for transfer to the plastid genome by homologous recombination, via a double crossover into the genome. The complete DNA sequence of the plastid genome of tobacco has been reported (Shinozaki et al. (1986) *EMBO J.* 5:2043–2049). Complete DNA sequences of the plastid genomes from liverwort (Ohyama et al. (1986) *Nature* 322:572–574) and rice (Hiratsuka et al. (1989) *Mol. Gen. Genet.* 217:185–194), have also been reported.

Where the regions of homology are present in the inverted repeat regions of the plastid genome (known as IRA and IRB), two copies of the transgene are expected per transformed plastid. The regions of homology within the plastid genome are approximately 1 kb in size. Smaller regions of homology may also be used, and as little as 100 bp can provide for homologous recombination into the plastid genome. However, the frequency of recombination and thus the frequency of obtaining plants having transformed plastids decreases with decreasing size of the homology regions.

Examples of constructs having regions of homology the plastid genome are described in Svab et.al. (1990 supra) and Svab et al. (1993 supra). Regions useful for recombination into tobacco and Brassica plastid genomes are also identified in the following examples, but homologous recombination and selection constructs may be prepared using many plastid DNA sequences, and to any target plant species. In the examples provided herein, the flanking tobacco plastid homology regions of the plastid expression construct direct the insertion of a *Bacillus thuringiensis* transgene into the tobacco genome between trnv and the rps12 operon. Since integration into the plastid genome occurs by homologous recombination and the target site is in an inverted repeat region of the plastid genome, two copies of the transgene per plastid genome are expected. Selection is made for the spectinomycin resistance marker phenotype expressed by the aadA gene.

In the examples the native cry gene, i.e., having an unmodified coding region to the protoxin, is placed into a plastid expression construct for expression of *Bacillus thuringiensis* toxin from the plant plastid.

A synthetic *Bacillus thuringiensis* gene is placed in the same expression construct as the protoxin gene. The synthetic gene is designed to have tobacco RuBPCO small subunit codon usage, with an overall increase in the guanine plus cytosine content to 55% (with respect to the native gene content of 39%), and has been truncated to leave only those sequences which enode the active fragment of the toxin. Such a gene is known to provide optimal expression from the plant nuclear genome. Both the bacterial gene which has been resynthesized for increased expression from plant nuclear transformation and the non-resynthesized, non-truncated wild-type gene to the protoxin are introduced via a chloroplast transformation vector (FIG. 1).

Unexpectedly, it is found that expression of the toxin is greatly enhanced from the native encoding sequence for the gene, as opposed to a version of the gene resynthesized to approximate the preferred codons of the plant genome. Tobacco lines containing the native encoding sequence demonstrate strong insecticidal bioactivity, as measured by insect feeding assays. Tobacco lines having a synthetic cryIA(c) gene demonstrate no observable bioactivity. As in both cases the constructs are introduced in a controlled manner by homologous recombination from the same plastid vector, the differences cannot be accounted for by positional effects.

In transformed plants containing the native encoding sequence, the *Bacillus thuringiensis* toxin is present as a component of up to about 5% or greater of the total leaf protein, a level which is much higher than is present in the leaf of plants resulting from nuclear transformation. In plants containing the gene resynthesized to approximate the preferred codons of the plant genome, the MRNA to the toxin appears degraded, and little or no toxin protein appears present in the leaf.

That a native *Bacillus thuringiensis* toxin gene is expressed to such a high level in the plastid, while an otherwise identical construct containing a *Bacillus thuringiensis* gene resynthesized for efficient nuclear expression is very poorly expressed in the plastid, despite having the same copy number in the plastid, suggests that the adenine plus thymine content of the plastid transgene heavily influences expression. As previously noted, the guanine plus cytosine content of the synthetic gene was increased to 55%, which is high relative to that of the plastid genome content of less than 40% guanine plus cytosine. This difference may cause inefficient processing of the mRNA, or lead to an increase in its rate of degradation. The native *Bacillus thuringiensis* gene has a guanine plus cytosine percentage which more closely matches that of the plastid genome, and thus more closely favors the codon usage of a plastid gene.

The adenine plus thymine content of the respective genes may not entirely explain the dramatic differences in expression of the native and synthetic *Bacillus thuringiensis* toxin proteins. One additional factor which could be postulated is that unwanted or highly inefficient plastid RNA processing signals are introduced into the synthetic czyIA(c) gene. Such signals, if present, could greatly reduce or even eliminate expression of the toxin.

In any case, it is now shown that the codon usage of the native *Bacillus thuringiensis* gene achieves an expression level which is much higher in plastid expression than is possible with resynthesized sequence to the same gene, thus demonstrating that a gene having bacterial codon usage can achieve high levels of expression in a plant plastid. The above results eliminate the need to resynthesize a certain class of genes for high level expression in plants.

The DNA sequence of interest may have a natural codon usage high in adenine and thymine, as is the case for the *Bacillus thuringiensis* gene, or may alternatively be resynthesized to enrich the adenine plus thymine content. In fact, while the constructs and methods described herein may be employed with a wide variety of native bacterial DNA encoding sequences, a wider range of potential gene targets for high level plastid expression can be obtained by resynthesizing genes, for instance plant nuclear genes, to increase the adenine and thymine content of the encoding sequence.

The invention now being generally described, it will be more readily understood by reference to the following examples which are included for purposes of illustration only and are not intended to limit the present invention.

EXAMPLES

In the experimental disclosure which follows, all temperatures are given in degrees centigrade (°), weights are given in grams (g), milligram (mg) or micrograms ($\mu$g), concentrations are given as molar (M), millimolar (mM) or micromolar ($\mu$M) and all volumes are given in liters (l), milliliters (ml) or microliters ($\mu$l), unless otherwise indicated.

Example 1

Plastid Transformation Vectors

Constructs and methods for use in transforming the plastids of higher plants are described in Svab et al. (1990 supra), Svab et al. (1993 supra) and Staub et al. (1993 supra). The complete DNA sequences of the plastid genome of tobacco are reported by Shinozaki et al. (1986 supra). All plastid DNA references in the following description are to the nucleotide number from tobacco.

The cryIA(c) gene is obtained from plasmid pBtkHD73 (Toagosei Chemical Co., Japan). This gene is further processed by digestion with SmaI/NsiI and a synthetic adapter is inserted (top strand: (SEQ ID NO: 1) 5'-CCCGGATCCATGGATAACAATCCGA-ACATCAATGAATGCA-3'; bottom strand; (SEQ ID NO: 2) 5'-TTCATTGATGTTCGGATT-GTTATCCATGGATCCGGG-3'). The entire 5' untranslated region from the cryIA(c) gene is then removed, and an NcoI site is introduced at the natural start codon (position 163 of the nucleotide sequence (Adang et al. (1985) *Gene* 36;289–300). A BamHI site is introduced just upstream of the NcoI site. Oligonucleotide mutagenesis is performed to introduce BglII and SalI sites directly adjacent to the stop codon of the cryIA(c) gene, to facilitate removal of unwanted DNA 3' of the coding region. The remaining sequence includes the entire encoding region to the protoxin.

A synthetic cryIA(c) gene encoding the active toxin fragment is constructed by annealing and ligating 70 and 90 base oligonucleotides, in a method as described (Wosnick et al. (1987) Gene 60;115–127). The synthetic gene is designed to have tobacco RuBISCO small subunit codon usage, including a guanine and cytosine content of 55%, with an NcoI site at the start codon and a SalI site at the stop codon, while still encoding the amino acid sequence of the toxin. This synthetic gene is also truncated, however, so that the encoding region only provides the amino acid sequence to the active fragment of the protoxin.

A plastid transformation vector is used which carries a passenger gene in a Prrn(L)rbcL(S)/Trps16 expression cassette, with polylinker restriction sites. The Prrn(L)rbcL (S) fragments are described in Svab et al. (1993 supra). To further secure the stability of the mRNAs, the Trps16 fragment is cloned downstream of the passenger gene encoding region. The Trps16 fragment comprises the rps16 gene 3'-regulatory region from nucleotides 5,087 to 4,939 in the tobacco plasmid DNA.

Chimeric genes are preferably inserted into the vector to direct their transcription towards the rrn operon. Thus, in the plastid genome, chimeric genes are transcribed from the Prrn(L)rbcL(S) 5'-regulatory region comprising the long rrn operon promoter fragment from nucleotides 102,561 to 102,677 of the tobacco plastid genome, which is fused with a synthetic leader sequence designed after the rbcL gene leader between nucleotides 57,569 to 57,584 in the plastid DNA.

The plastid transformation vector also carries a selectable spectinomycin resistance gene (aadA) under control of psbA gene expression signals. The regulatory and encoding sequences are also flanked by plastid DNA homology regions whose limits are bp 138,447 (EcoRI) to 140,219 (HincII) and 140,219 (HincII) to 141,382 (BglII) of the tobacco plastid genome (Shinozaki et al. (1986 supra)). This directs insertion of foreign genes located between the flanking regions into the plastid between the trnV gene and the rps12/7 operon.

This plastid transformation vector is digested with the NcoI/SalI restriction endonucleases to remove the encoding region of the passenger gene, which is then replaced with a NcoI/SalI fragment containing the synthetic cryIA(c) coding region, yielding a vector which is designated pZS223 (FIG.

1). The wild type cryIA(c) protoxin gene is similarly cloned as an NcoI/SalI fragment, yielding a plasmid designated pZS224. By this approach *Bacillus thuringiensis* DNA 3' of the protein coding region is omitted for both plasmids, pZS223 and pZS224.

The insertion of the respective cry genes from vectors pZS223 and pZS224 into the wild-type plastid genome (Nt-ptDNA) to yield transplastomes Nt-pZS223 and Nt-pZS224, respectively, is shown in FIG. 1. The abbreviations used in FIG. 1 are as follows: 16S, 16S rRNA gene; trnV, trnV gene; aada, spectinomycin resistance gene; cry1A and cry73 are synthetic and native *Bacillus thuringiensis* d-endotoxin genes, respectively. The restriction endonuclease cleavage sites are designated as follows: B, BamHI; Bg, BglII; H, HindIII; N, NcoI; RI, EcoRI, RV, EcoRV; S, SalI.

Example 2

Plant Plastid Transformation

Stable transformation of tobacco plastid genomes by particle bombardment is reported in Svab et.al. (1990 supra) and Svab et al. (1993 supra). The methods described therein may be employed to obtain plants transformed with the plastid expression constructs described herein. Such methods generally involve DNA bombardment of a target host explant, preferably an explant made from a tissue which is rich in metabolically active plastids, such as green plant tissues including leaves or cotyledons.

Tobacco seeds (*N. tabacum* v. Xanthi N/C) are surface sterilized in a 50% chlorox solution (2.5% sodium hypochlorite) for 20 minutes and rinsed 4 times in sterile $H_2O$. These are plated asceptically on a 0.2×MS salts media and allowed to germinate. The seedlings are grown on agar solidified MS media with 30 g/l sucrose (Murashige et al. (1962) *Physiol. Plant* 15:493–497).

Tungsten microprojectiles (1.0 $\mu$M) are coated with plasmid DNA according to Maliga (Maliga, P. (1993) Methods in Plant Molecular Biology—A Laboratory Manual, eds. Pal Maliga, Daniel Klessig, Anthony Cashmore, Wilhelm Gruissem and Joseph Varner; Cold Spring Harbor Press) and used to bombard mature leaves, placed abaxial side up on RMOP media; MS salts, 1 mg/l BAP, 0.1 mg/l NAA, 30 g/l sucrose and 0.7% phytagar. Svab et al. (1990) *Proc. Natl. Acad. Sci. USA* 87:8526–8530 (using the Bio-Rad PDS 1000 He system (Sanford et al., An improved, helium-driven Biolistic device, *Technique* 3:3–16)). Plasmids pZS223 and pZS224 are used as the coating plasmid DNA.

The bombarded tissue is then cultured for approximately 2 days on a cell division-promoting media, after which the plant tissue is transferred to a selective media containing an inhibitory amount of the particular selective agent. Transformed explants form green shoots in approximately 3–8 weeks. Leaves from these shoots are then subcultured on the same selective media to ensure production and selection of homoplasmic shoots.

Example 3

DNA Gel Blot Analysis of Transplastomic Lines

Transformed plants selected for marker aadA marker gene expression are analyzed to determine whether the entire plastid content of the plant has been transformed (homoplastic transformants). Typically, following two rounds of shoot formation and spectinomycin selection, approximately 50% of the transgenic plantlets which are analyzed are homoplastic, as determined by Southern blot analysis of plastid DNA. Homoplasmic plantlets are selected for further cultivation.

Following a second round of shoot formation and spectinomycin selection, two transplastomic lines for each construct are obtained, Nt-pZS223 and Nt-pZS224. These lines are checked for homoplasmy. Southern blot analysis is used to confirm the integration of the chimeric cry genes in the tobacco plastid genome. Preparation, electrophoresis, and transfer of DNA to filters is as described (Svab et al., (1993 supra)).

The complete disappearance of the 3.3 Kb native tobacco BamHI fragment in the Nt-pZS223 and Nt-pZS224 transformants with a probe covering the region of integration, and the appearance of expected sized bands for the inserted DNA fragments in those transformants, 5.5 kb and 7.3 kb, respectively (see FIG. 1), establishes that the transformed plants are homoplasmic for the intended constructs. Probing identical filters with the aada, cryIA(c) protoxin, and synthetic cryIA(c) genes demonstrated a linkage of the aadA and cryIA(c) genes to the expected 5.5 and 7.3 Kb BamHI fragments as well as the lack of these genes in the negative control.

Example 4

Insect Bioassays

As described, the development of transformed plant lines NtpZS223 and Nt-pZS224 is accomplished on RMOP media supplemented with 500 mg/l Spectinomycin dihydrochloride. Plants are subcloned on the same selective medium, by the method according Svab et al.(1990 supra). Selected plants are then rooted in MS media containing 1 mg/l IBA, 500 mg/l Spectinomycin dihydrochloride and 0.6% phytagar.

*Helicoverpa zea* and *Heliothis virescens* eggs are obtained from the USDA-ARS in Stoneville, Miss. and allowed to hatch. Neonate larva are placed on Tobacco Budworm Diet from Bioserve (Frenchtown, N.J.), and incubated in a 16:8 photoperiod at 28° C. for 5 days. The larva develop during this time to late second or early third instar.

At 5 days, fully expanded leaves are excised from the tobacco plants and placed on 3 ml of 2% agar in a 32 well rearing tray from CD International (Pitman, N.J.). The larva are placed 1 per well, sealed and incubated for 5 days at the same conditions. At day 10, the leaf material consumed by the insect is estimated and insects checked for mortality. The larva are considered dead if they showed no movement after prodding with forceps.

Example 5

Insecticidal Feeding Activity

To determine the presence and relative amount of active *Bacillus thuringiensis* d-toxin in the tobacco lines homoplasmic for native protoxin and synthetic 'truncated' cryIA(c) gene expression constructs, efficacy of these plants to third instar *Heliothis virescens* (tobacco budworm) and *Helicoverpa zea* (corn earworm/cotton bollworm) larvae is tested (See table). Both test insects are sensitive to the cryIA(c) toxin with *H. zea* being 10-fold more resistant than *H. virescens* (MacIntosh et al. (1990) *J. Invertebr. Pathol.* 56:258–266.).

Third instar larvae are chosen for the bioassay since the insects are more resistant to the toxin at this stage than are first instar larvae thus allowing a more stringent comparison between the control and test plants. Tobacco lines designated 4083 and 4084, derived by nuclear transformation with the same synthetic cryIA(c) gene as used in pZS223 and shown to be highly toxic to third instar *H. virescens* larvae, are used as positive controls in the bioassay. *Nicotiana tabacum* var. 'Petite Havana' serves as the negative control since this is the genetic background used to generate the transplastomic lines.

Table 1 is a summary of *Bacillus thuringiensis* tobacco insect feeding assays. The data demonstrates that transplastomic line Nt-pZS224 is very toxic to both *H. virescens* and *H. zea* as it causes 100% mortality to these insects while sustaining less than 2% total leaf damage. This result compares favorably to the results for positive control 4083 and 4084 tobacco plants. The 4083-2-4 plant when assayed with *H. zea* causes 100% mortality but sustains a much greater level of leaf feeding damage than the Nt-pZS224 tobacco line indicating less toxin production. Tobacco line 4084-4-1 performed comparably to Nt-pZS224 tobacco in feeding, although it does not compare to the levels of toxin produced in Nt-pZS224 when measured as a component of total leaf protein.

Tobacco line Nt-pZS223 shows no detectable bioactivity.

TABLE 1

SUMMARY OF BT TOBACCO INSECT FEEDING ASSAYS

| | Vector | plants tested | *Heliothis virescens*^^ | % Leaf eaten | *Hetiocoverpa zea*^^ | % Leaf eaten |
|---|---|---|---|---|---|---|
| | | | Chloroplast | | | |
| synthetic toxin gene | pZS223 | 223-3 | NO mortality | 100% | NO mortality | 100% |
| | | 223-5 | NO mortality | 75% | NO mortality | 100% |
| | | 223-12 | NT | | NO mortality | 100% |
| | | 223-13 | NO mortality | 75% | NT* | |
| wild type protoxin gene | pZS224 | 224-5 | 100% mortality | 2% | 100% mortality | 2% |
| | | 224-9 | 100% mortality | 2% | 100% mortality | 2% |
| | | | Nuclear Controls | | | |
| synthetic toxin gene | pCGN4083 | 4083-1-2 | 100% mortality | 2% | NT* | |
| | | 4083-2-4 | NT | | 100% mortality | 40% |
| | pCGN4084 | 4084-8-5 | 100% mortality | 2% | NT* | |
| | | 4084-1-1 | NT | | 100% mortality | 2% |
| | | | Untransformed Controls | | | |
| | | control 1 | 25% mortality | 75% | NO mortality | 100% |
| | | control 2 | NO mortality | 100% | NT* | |
| | | control 3 | 50% mortality | 75% | NT* | |

^^10 third instar larva were individually tested per plant
*NT: Plant not tested All publications and patent applications mentioned in this specification are indicative of the level of skill of those skilled in the art to which this invention pertains. All publications and patent applications are herein incorporated by reference to the same extent as if each individual publication or patent application is specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A construct comprising the following as operably joined components in the 5' to 3' direction of transcription:
   (a) a promoter functional in a plant plastid;
   (b) a DNA sequence encoding a peptide of interest; and
   (c) a transcription termination region that terminates transcription in a plant plastid,
   wherein said DNA sequence encoding said peptide of interest is derived from the nuclear genome of a plant cell, and wherein said DNA sequence encodes the same amino acid sequence as the native DNA sequence but has an enriched adenine and thyrmine content of greater than 50%.

2. The construct according to claim 1, wherein said construct further comprises:
   (d) a gene encoding a marker for selection of transformed plant cells; and
   (e) DNA regions of homology to the genome of said plastid,
   wherein said plant cells comprise a plastid that expresses said marker and wherein said DNA regions of homology flank said regions (a), (b), (c) and (d) of said construct and provide for homologous recombination into the plastid genome.

3. The construct according to claim 1 wherein said plant plastid is a chloroplast.

4. The construct according to claim 1 wherein said DNA sequence approximates the adenine and thymine content of a plant plastid genome.

5. The construct according to claim 2, wherein said marker confers resistance to spectinomycin and/or streptomycin.

6. A method for producing a peptide of interest in a solanaceous plant cell, said method comprising expressing said peptide in plastids of said solanaceous plant cell by transforming said plant cell with the construct according to claim 1.

7. The method of claims 6, wherein said construct further comprises:
   (d) a gene encoding a marker for selection of solanaceous plant cells; and
   (e) DNA regions of homology to the genome of said plastid,
   wherein said solanaceous plant cells comprise a plastid that expresses said marker, and wherein said said DNA regions of homology flank said components (a), (b), (c) and (d) of said construct and provide for homologous recombination into the plastid genome.

8. The method according to claim 6, wherein said plastids are chloroplasts.

9. The method according to claim 7, wherein said marker confers resistance to spectinomycin and/or streptomycin.

* * * * *